United States Patent [19]

Bauer et al.

[11] Patent Number: 4,745,759
[45] Date of Patent: May 24, 1988

[54] KIDNEY PRESERVATION MACHINE

[76] Inventors: Dan O. Bauer, 277 Kenwood Rd.;
Neal W. Bauer, 275 Merriweather,
both of Grosse Pointe Farms, Mich.
48236

[21] Appl. No.: 945,641

[22] Filed: Dec. 23, 1986

[51] Int. Cl.⁴ ............................................. F25B 21/02
[52] U.S. Cl. .............................................. 62/3; 62/64;
62/127; 62/376; 435/1
[58] Field of Search .................... 435/1; 62/3, 64, 126,
62/127, 376

[56] References Cited

U.S. PATENT DOCUMENTS

| | | | |
|---|---|---|---|
| 3,293,868 | 12/1966 | Gonzalez | 62/3 |
| 3,406,531 | 10/1968 | Swenson et al. | 435/1 X |
| 3,545,221 | 12/1970 | Swenson et al. | 435/1 X |
| 3,632,473 | 1/1972 | Beizer et al. | 435/1 |
| 3,753,357 | 8/1973 | Schwartz | 435/1 X |
| 3,810,367 | 5/1974 | Peterson | 435/1 X |
| 3,995,444 | 12/1976 | Clark et al. | 62/376 X |
| 4,186,565 | 2/1980 | Toledo-Pereyra | 435/1 X |

Primary Examiner—William E. Tapolcai
Attorney, Agent, or Firm—Brooks & Kushman

[57] ABSTRACT

Apparatus for maintaining extracorporeal organs in viable state during transportion and storage comprises a readily manually transportable insulated enclosure including separable cover and base portions, a perfusate reservoir in the enclosure, thermoelectric means in the base portion for cooling the reservoir and interior of the enclosure, means in the enclosure for supporting an organ for perfusing, means in the enclosure for directing perfusate expelled from the organ to the perfusate reservoir, a perfusate pump on the base portion for connection between the reservoir and an organ supported within the enclosure, and control means for varying the operation of the pump and thermoelectric means to maintain the temperature and flow of the perfusate being pumped within predetermined limits.

14 Claims, 9 Drawing Sheets

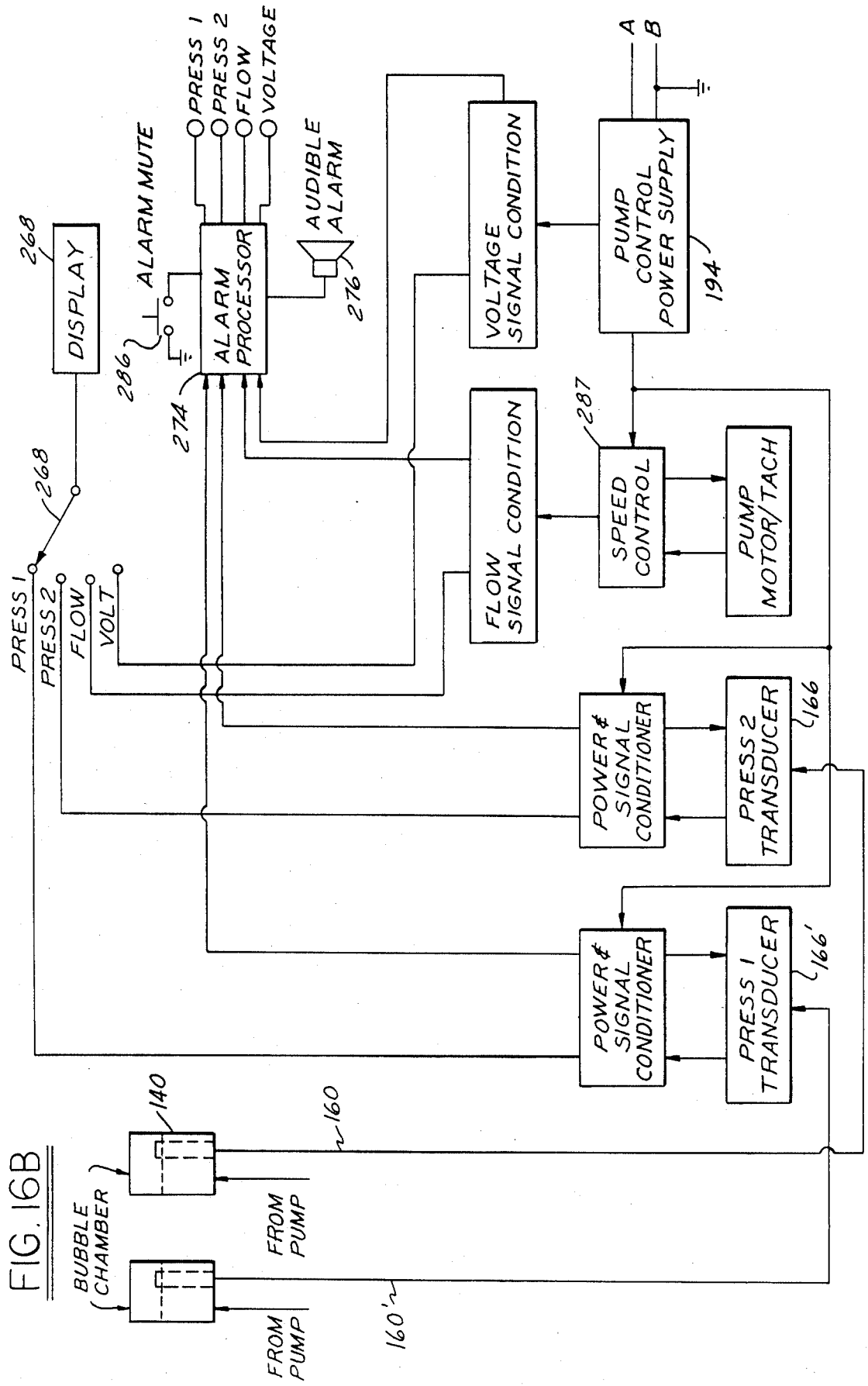

KIDNEY PRESERVATION MACHINE

FIELD OF INVENTION

This invention relates to a machine for preserving a donated organ, such as a human kidney, until transplanted.

BACKGROUND OF THE INVENTION

As improvements in transplantation of human organs advance, there is a growing need for preserving a donated organ until it is transplanted. Because the location of the organ at the time of donation may be a considerable distance from the location where the transplant is to be made, it is necessary to preserve the organ while transporting it to, or holding it at, the place of transplant. Heretofore several efforts have been made, as represented by the following United States Patents, to preserve donated organs and in some instances to allow for the transportation of the donated organ, but, for the most part, such prior art devices have not been wholly satisfactory for several reasons. Patent disclosures representative of such art are as follows, U.S. Pat. Nos.:

3,881,990
3,935,065
4,186,565
4,242,883
4,299,919
4,395,492
4,411,652
4,462,215
4,471,629
4,473,637
4,494,385

My research has indicated that the prior art has failed to adequately address the problem of providing a compact, highly mobile and essentially self-contained machine which will permit the preservation of a donated organ, such as a human kidney, for the time required to transport it to the donee's location and which controls the temperature, pressure and flow rate of the perfusate and provides suitable alarms when operating conditions depart from the prescribed parameters.

SUMMARY OF THE INVENTION

The invention disclosed herein is embodied in a portable machine which may be manually carried and transported by automotive vehicle, airplane, or the like, and may be operated by a portable battery pack in the absence of a suitable source of 110 V alternating current. The machine is capable of perfusing one or more organs in a temperature controlled, essentially isolated environment. A thermoelectric refrigeration system regulates the temperature of the perfusate delivered to the organ. The temperature of the perfusate is automatically controlled within selectable parameters by microprocessor circuitry. An alarm system calls attention to changes in temperature, pressure, flow and voltage parameters that exceed select conditions. A nonpulsatile perfusate pump is capable of delivering perfusate at a closely controlled rate and pressure to the donated organ and is operable to provide perfusate independently to each of two organs stored in the machine.

DESCRIPTION OF THE DRAWINGS

FIGS. 16A and 16B are schematic diagrams of the power supply and control circuitry for the machine.

BRIEF DESCRIPTION OF PREFERRED EMBODIMENT

Figure 1:
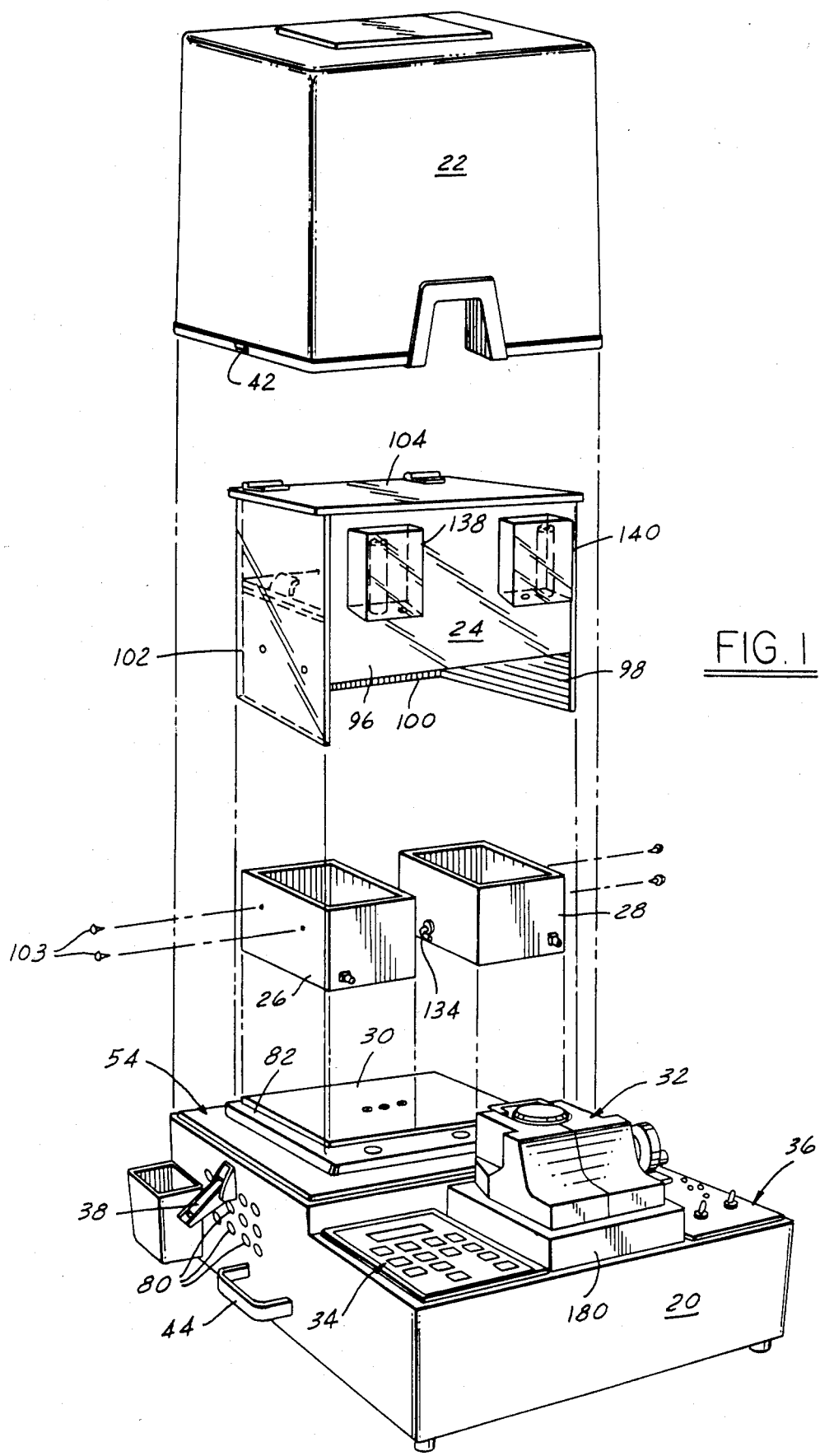
FIG. 1 is a perspective exploded view of a machine embodying the invention.
Figure 2:
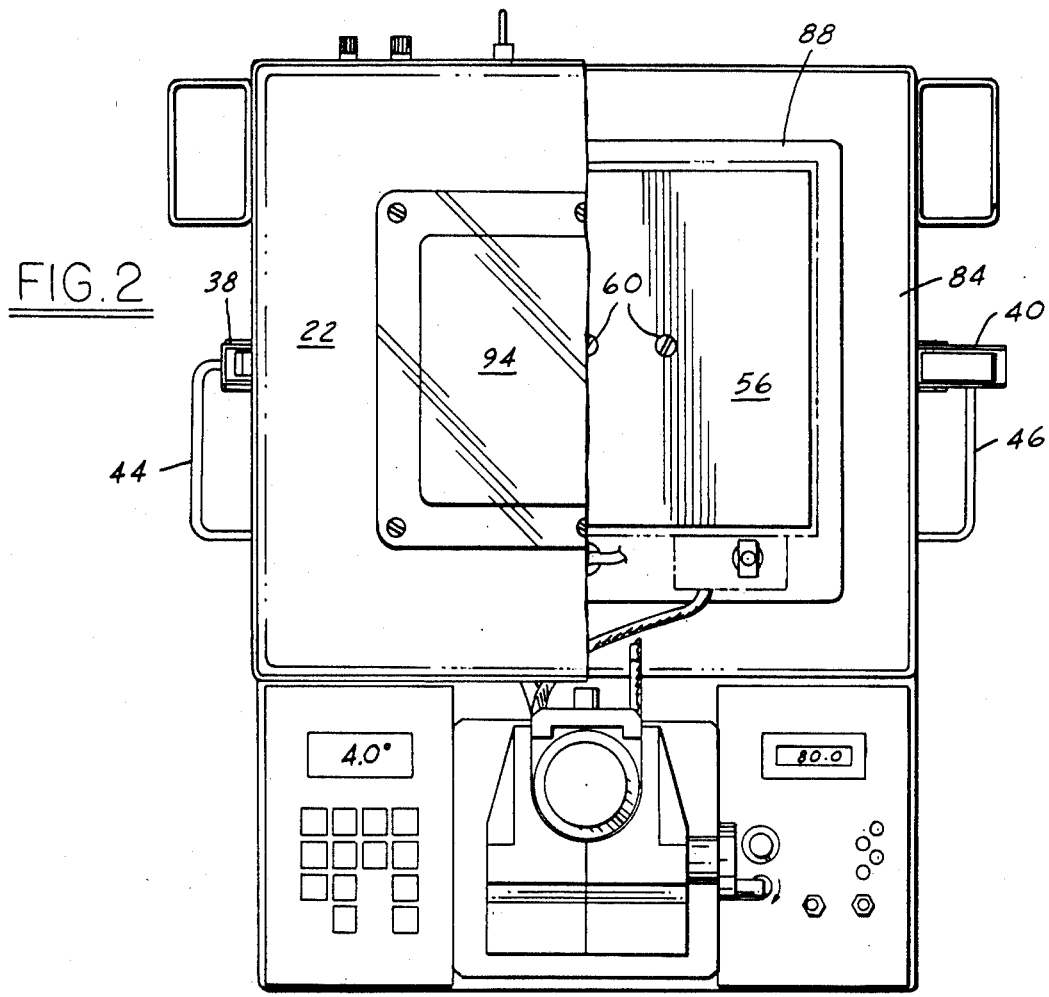
FIG. 2 is a top plan view of the machine of FIG. 1 with parts broken away for clarity.

As shown in FIG. 1, a machine embodying the invention includes a hollow base member 20, a removable cover member 22 receivable on the base member and removably enclosing a transparent organ receiving cassette 24 surmounting a pair of perfusate reservoirs 26 and 28, intended to rest on an upwardly facing cold plate 30 on the base member. A nonpulsatile perfusate pump 32 is mounted on the base between a temperature controller keyboard 34 and a pump controller keyboard 36. Conventional over-center locks 38 and 40 (shown in FIG. 2) engaging hooks 42 (one of which is shown in FIG. 1) serve to removably secure the cover to the base. Carrying handles 44 and 46 (shown in FIG. 2) enable the machine to be manually picked up for transport.

The hollow base 20 opens at the bottom through a removable panel 48 (see FIG. 6) which is held in any suitable fashion to the sidewall 50. Rubber feet or the like 52 may be provided for supporting the machine above a surface on which it may be rested and provide ample volume for air intake for the thermoelectric refrigerator heat exchanger. The hollow interior of the base is intended to house the pump motor, thermoelectric refrigeration modules, power supply and microprocessor control circuitry shown in FIGS. 16A and 16B.

Figure 6:
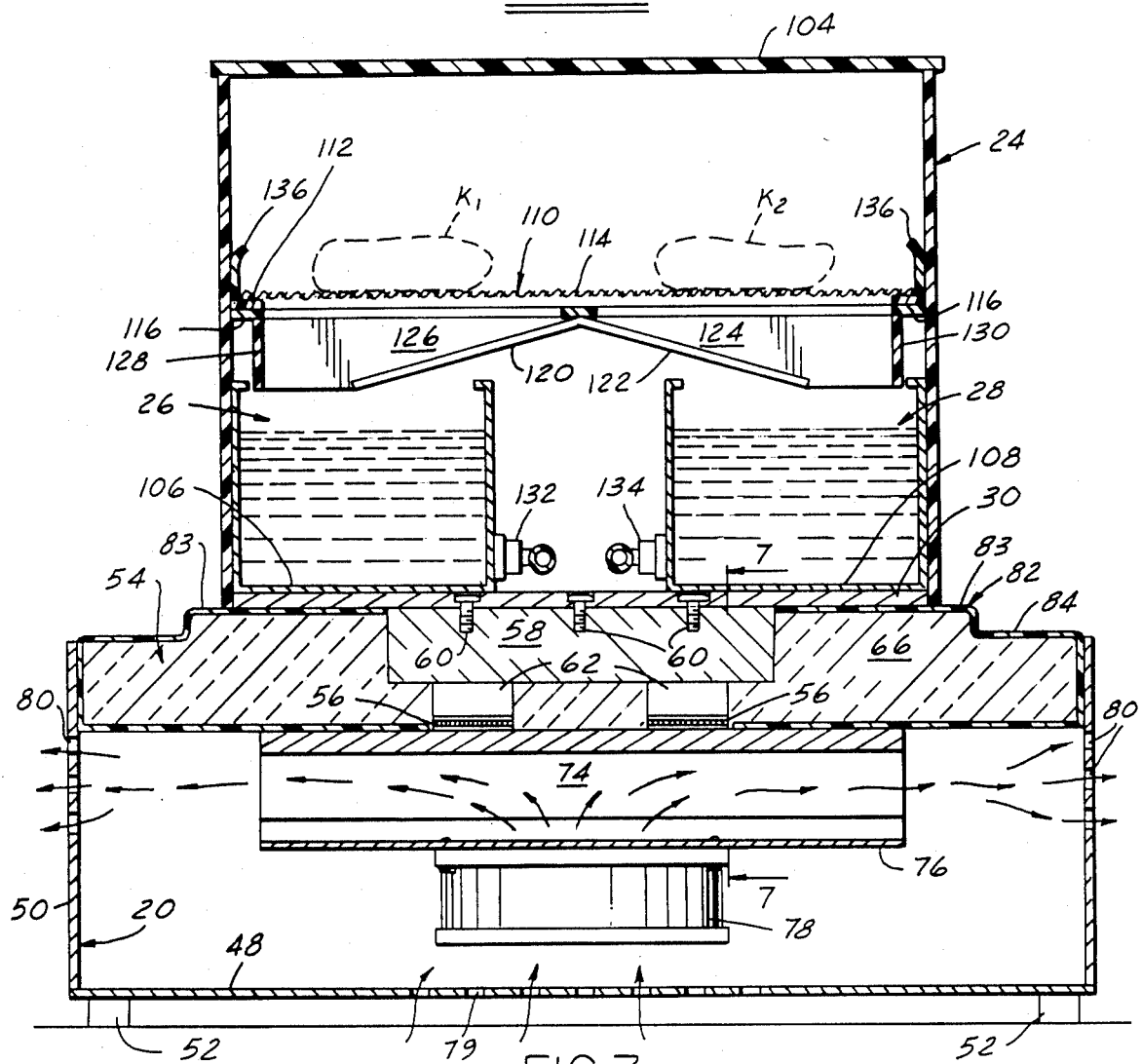
FIG. 6 is a cross sectional view taken substantially on the line 6—6 of FIG. 4.
Figure 7:
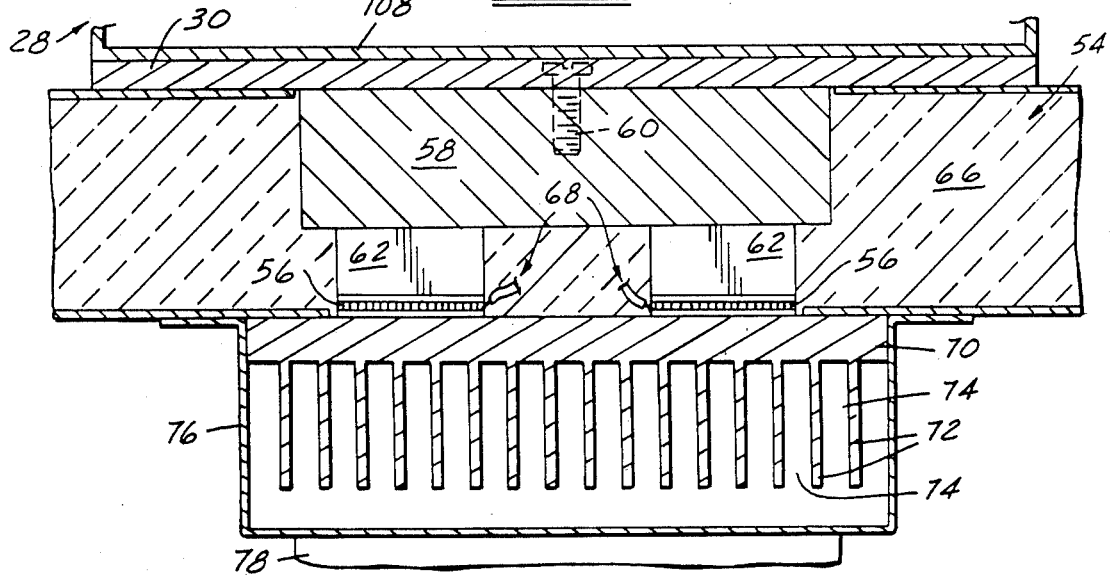
FIG. 7 is a cross sectional view through the thermoelectric cooler taken substantially on the line 7—7 of FIG. 6.

The front top half of the base is stepped down slightly to support the control panels 34 and 36, as well as the nonpulsatile pump, while the rearward half of the base is raised slightly to support the perfusate reservoirs, cassette and cover. As shown in FIGS. 1, 6 and 7, a thermally insulated panel 54 is mounted in the top of the rear half of the base and secured therein in any suitable fashion. Overlying the panel 54 but marginally spaced from the edge thereof is an upwardly facing heat transfer surface or cooling plate 30 formed of a good heat conductive material such as aluminum or stainless steel. The plate 30 is secured in heat transfer relation to a heat sink block of aluminum or the like 58 by the fasteners 60, which in turn is also secured in heat transfer relation to a plurality of heat transfer blocks, 62. A plurality of thermoelectric modules 56 are disposed in heat transfer relation against the underside of the heat transfer blocks, 62. These thermoelectric modules are of conventional construction and may be obtained from Materials Electronic Products Corporation of 990 Spruce Street, Trenton, N.J. 48648, or from the Borg-Warner Corporation, as well as others. These modules operate on the Peltier Effect, whereby upon application of a direct current thereto, a temperature gradient through the cell is created such that one side thereof will be cooler and the other side warmer. In the disclosed embodiment the cooled sides of the cells are placed in heat transfer relation with the heat transfer blocks 62 such that heat within the block 58 will pass out of the block through the thermoelectric modules, thereby lowing the temperature of the heat sink and in turn the cooling plate 30.

Insulation 66 within the panel 54 surrounds the heat sink 58, heat transfer blocks 62 and modules 56 as best shown in FIG. 7. Electric conductors 68 are connected to the thermoelectric modules and extend through the insulation. Disposed in heat transfer relation with the warm side of the thermoelectric module 62 is a finned heat exchanger 70 whose fins 72 are arranged to provide elongated pair passageways 74 opening at opposite ends through an enclosing shroud 76. An electric fan 78 secured to the bottom of the shroud 76 draws in air from the ambient air external to the machine through provided apertures 79 in panel 48 and blows it through the air passages 74 between the fins 72 from whence the heated air passes out through the side walls 50 through the provided apertures 80.

Figure 3:
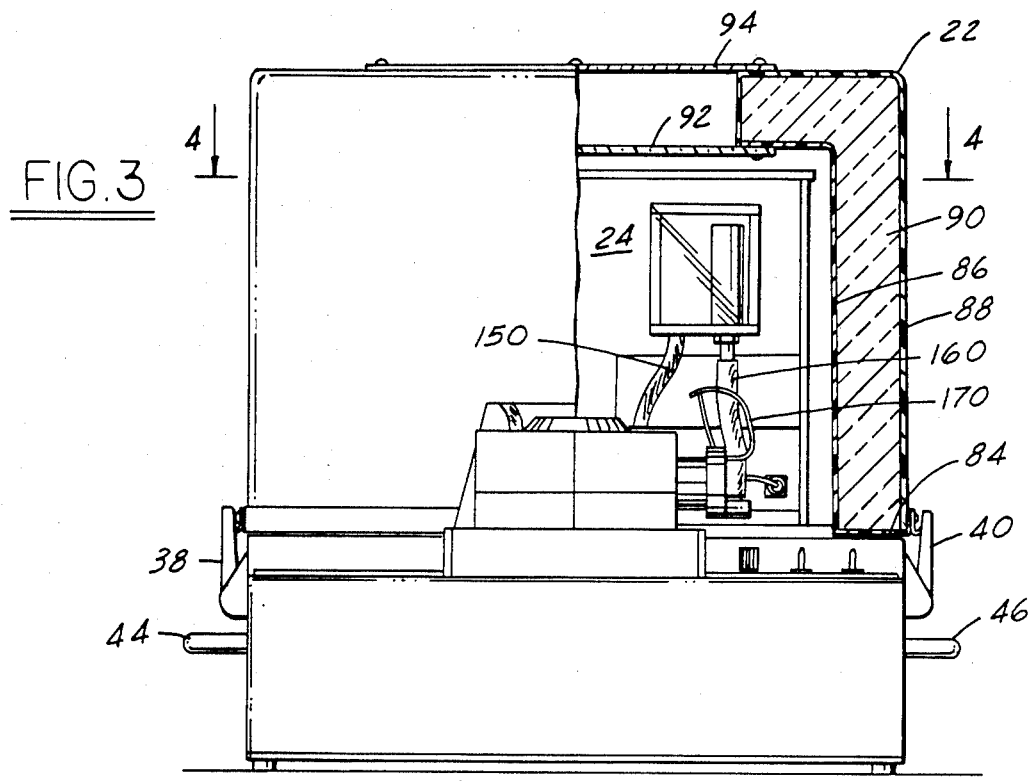
FIG. 3 is a front elevation of the machine with the cover partially broken away.

It will be noted that the cooling plate 30 rests on a slightly raised portion 82 of the insulated panel 54 with the perimeter of the cooling plate spaced from the perimeter of such raised portion to provide a cassette supporting ledge 83. Portion 82 is itself spaced from the marginal edges of the panel 54 to provide a circumferentially extending supporting ledge 84 around the heat transfer surface or cooling plate 56 in outwardly spaced relation therefrom. The ledge 84 is intended to support the cover 22 as best shown in FIG. 3.

The cover is generally box shaped with an open bottom. Inner and outer spaced apart walls 86 and 88 have insulation 90 therebetween. Centrally at the top of the cover is a window formed by a pair of transparent plates 92 and 94 secured to the inside and outside walls of the cover permitting visual inspection of stored organs without removal of the cover.

The cover 22 and base panel 54 cooperatively provide an insulated storage compartment adapted to receive the organ cassette 24. The cassette comprises four interconnected side walls 96, 98, 100 and 102, and is provided with a hinged lid 104. The cassette is preferably formed of autoclavable transparent plastic. The walls 98, 100 and 102 are adapted to rest on the ledge 83 surrounding the cold palte 30 just inside ledge 84 to support the cassette on the base member. Removably secured as by fasteners 103 to the side walls of the cassette are stainless steel reservoirs 26 and 28 each having an encircling side wall and a bottom wall. The bottom walls 106 and 108 lie in flush heat transfer relation with the cold plate 30 as best shown in FIGS. 6 and 7. Tube fittings 132 and 134 are mounted on the side wall of each reservoir to receive perfusate from the reservoir.

Disposed in spaced relation above the reservoirs within the cassette is a removable organ supporting tray 110 comprising an encircling frame 112 spanned by a nylon mesh or the like 114 on which the organs $K_1$ and $K_2$ may be placed for support above the reservoirs. The mesh will permit ready passage of perfusate expelled from the organs downwardly to the reservoirs. To guide the perfusate from the mesh down into the reservoirs, a pair of deflectors 120 and 122 are provided. The deflectors extend between a pair of opposed depending skirts 124 and 126 secured to the underside of the tray supporting ledge 116. A pair of depending skirts 128 and 130 extend between the pairs of skirts 124 and 126 spaced from the ends of the deflectors 120 and 122 as shown particularly in FIG. 6. The skirts and deflectors serve to guide the perfusate from the organs $K_1$ and $K_2$ into the reservoirs as aforesaid such that the perfusate from one organ is not commingled with the perfusate from the other organ. The construction of the cassette is such that it may be readily cleaned, as in an autoclave, and for this purpose the reservoirs 26 and 28 may be detached therefrom. The organ supporting tray 110 may be provided with handles 136 to facilitate removal from the cassette and thereby enabling the filling of the individual reservoir with perfusate.

At the front of the cassette, mounted on the wall 96, are a pair of bubble chambers 138 and 140. A description of one chamber will suffice for both. Primed reference numerals indicate like parts. The chambers are completely enclosed by side, top and bottom walls and are integral with the end wall 96 of the cassette and are formed of transparent autoclavable plastic. Through the bottom wall 142 extends a pair of fittings 144 and 146, the former being adapted to receive the outlet end of the pump hose or tube 150. The opposite end of such pump tube is connected to the outlet fitting 134 on reservoir 28. Thus, there is a pump tube 150 extending from the outlet fitting 134 on the reservoir 28 to the inlet fitting 144 at the bottom of the bubble chamber 140. Similarly, a pump hose 150' extends from the fitting 132 of reservoir 26 to the fitting 144' of the bubble chamber 138.

The fitting 146 communicates with the inside of a riser tube 156 whose upper end is spaced below the top wall 158 of the bubble chamber so that the interior of the tube is exposed to the trapped air pressure within the bubble chamber. The normal level of perfusate in the bubble chamber will lie between the outlet fitting opening through the wall 96 into the bubble chamber and the top of the tube 156, thus, perfusate will not normally enter the tube 156 though it will be subjected to the same pressure as exists within the bubble chamber. The air space above the level L of perfusate in the bubble chamber will provide a place for any entrained air bubbles in the perfusate to escape before entering the organ. Fitting 146 is connected by a pressure transmitting tube 160 to the pressure transducer 166 as shown in FIG. 16B. Similarly, a pressure transmitting tube 160' extends from the bubble chamber 138 to the pressure transducer 166'.

Each of the reservoirs 26 and 28 is provided with a temperature probe receiving well 163 (and 163') for removably receiving the temperature probe 162 which is connected to the signal processor within the temperature controller by the conductor 168. Thus, the temperature of perfusate in either of the reservoirs may be monitored.

Figure 4:
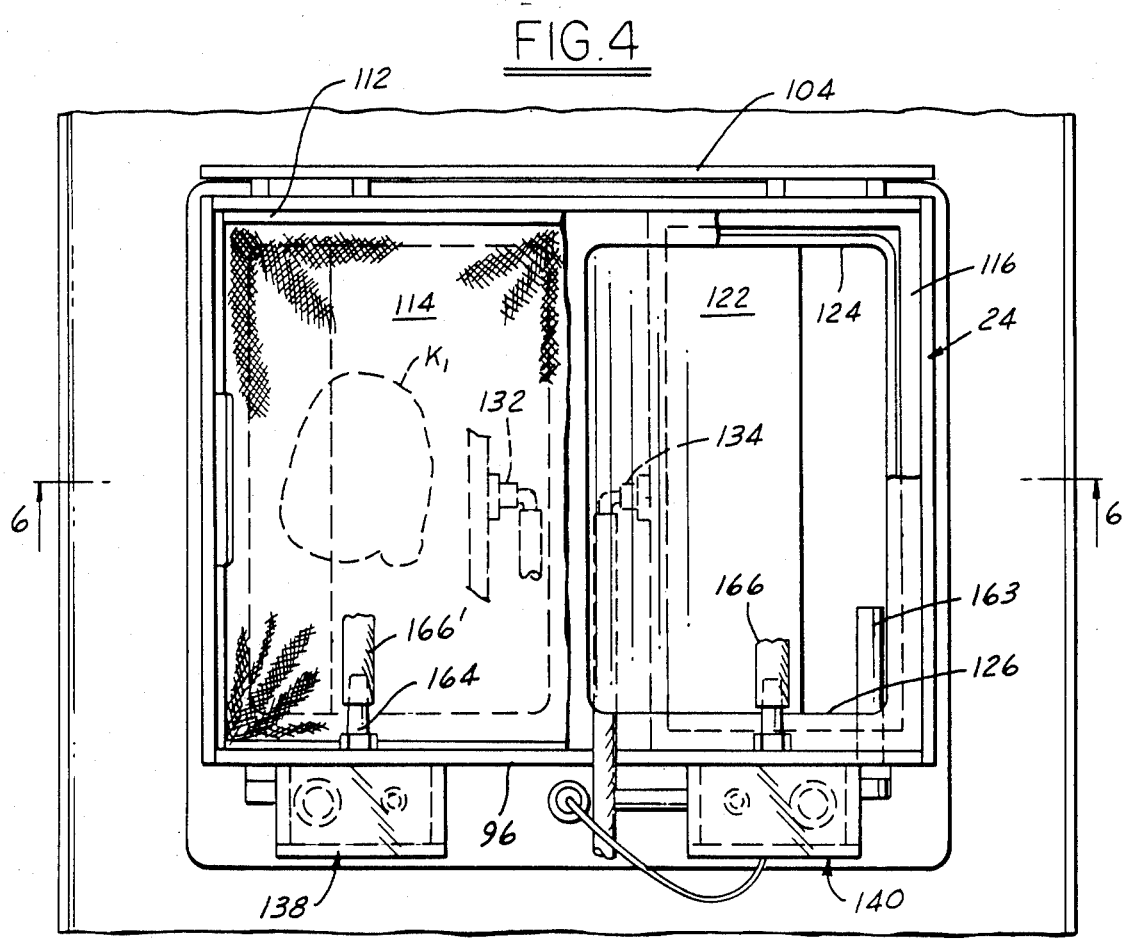
FIG. 4 is a cross sectional view taken substantially on the line 4—4 of FIG. 3 and showing in phantom outline a kidney in the left side of the cassette.
Figure 5:
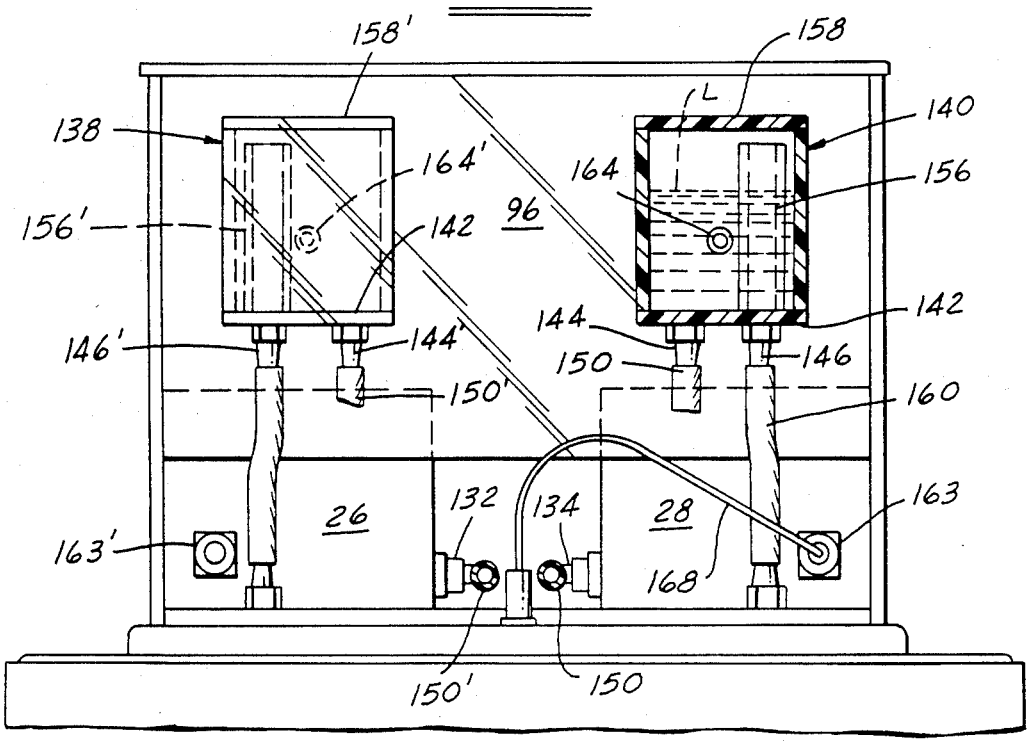
FIG. 5 is a front elevation of the cassette with one of the bubble chambers in section.

A fitting 164 opens through the wall 96 into the bubble chamber and is intended to be connected by a perfusate delivery tube 166 to the organ, such as $K_1$, shown in phantom outline in FIG. 4. The tube 166' shown in FIG. 4 is to be connected to the organ to deliver the perfusate to the organ from the bubble chamber. It will be apparent that the pressure read by transducer 166 will be approximately that of the perfusate as it is delivered to the organ $K_1$.

If desired, a conduit pressure clamp 170 may be placed on the pressure delivery tube 160 to block the transmission of pressure between the bubble chamber and the pressure sensor.

The pressure clamp serves as a safety device to prevent the perfusate from migrating into the pressure transducer as would occur if an air leak were to develop in the bubble chamber or connecting pressure transducer tubes and/or fittings.

The perfusate pump 32 is best shown in FIGS. 8-13 inclusive. It is of the nonpulsatile type. The pump is adapted to receive the perfusate conduits 150 and 150' extending between the fittings 132 and 134 on the reservoirs and their respective bubble chambers 138 and 140, and to pump the perfusate from the reservoir to the bubble chamber and thence to the organ being preserved in the machine. The pump is of the roller type. Loading or unloading of the tubes may be effected without requiring any disassembly of the pump and without contaminating the tubes. Either the tube 150 or the tube 150', or both, may be inserted in the pump such that either one or both reservoirs may be connected to the pump for perfusing one or two organs.

Figure 8:
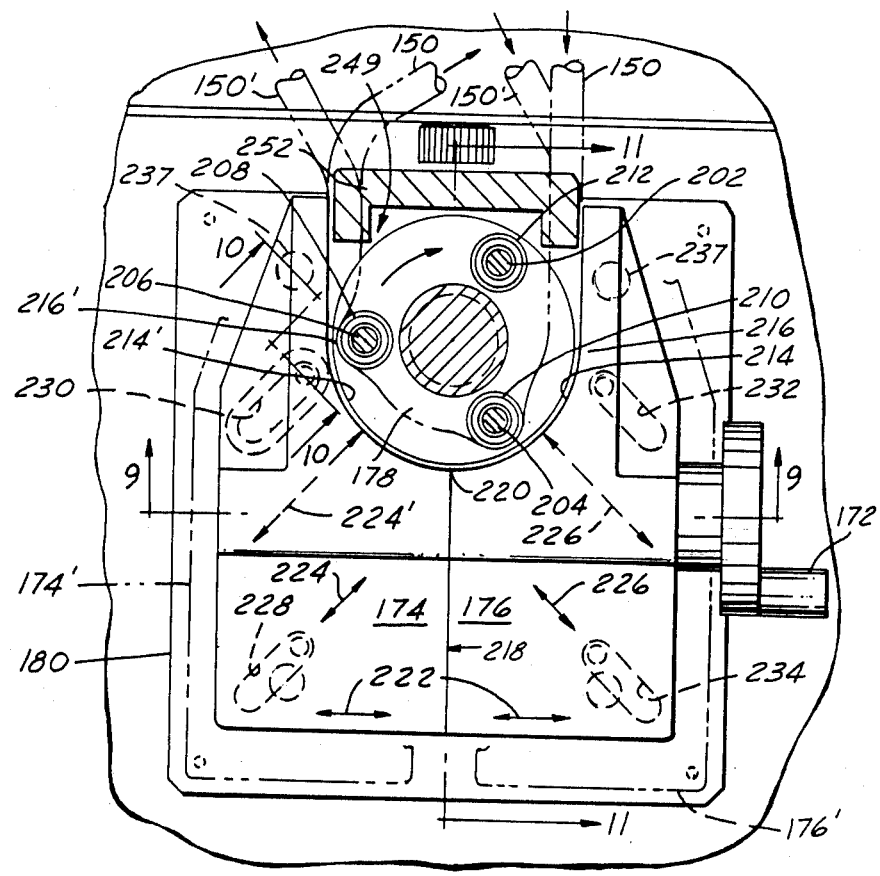
FIG. 8 is a top view of the perfusate pump with portions removed for clarity.
Figure 12:
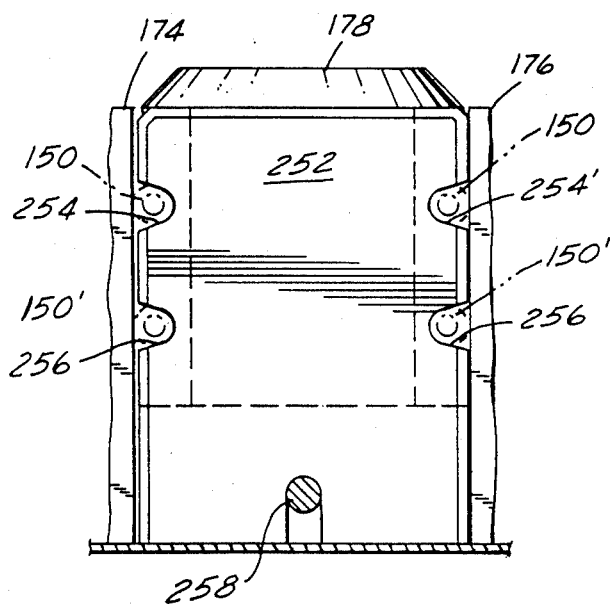
FIG. 12 is an end view taken on the line 12—12 of FIG. 11.

To place the tubes 150 and 150' in the pump, the handle 172 is cranked to open the pump by moving the pump halves 174 and 176 from either solid outline positions in the direction of the arrows in FIG. 8 to their phantom outline positions 174' and 176', thereby opening a space between the pump halves and the roller assembly 178. The tubes 150 and 150' may then be disposed between the roller assembly and the pump halves, as best shown in FIGS. 8 and 12. The handle 172 is then reversely cranked to close the pump halves to the solid outline position of FIG. 8. Upon rotation of the roller assembly, the tubes 150 and 150' are squeezed by the roller assembly to cause a pumping action through the tubes.

The construction of the pump includes a base 180 adapted to be mounted on the base member 20 of the machine. A vertical bore in the base 180 receives a bearing assembly 182 carrying the stub shaft 184 which is an integral extension of the rotor shaft 186. The lower end of the stub shaft 184 is adapted to receive in driving engagement the drive lug 188 projecting from the drive unit 190. Unit 190 may comprise a direct current servo motor 192 to be driven by the pump control power supply 194 ref. FIG. 16B. A right angle transmission 196 is connected between the motor and driving lug 188. A shaft seal may be provided at 197 to prevent the entry of contaminate into the bearing assembly.

The rotor shaft 186 includes opposing flange portions 198 and 200 rigidly connected thereto. Extending between the flanges in equidistantly spaced parallel relation are three roller supporting spindles 202, 204 and 206, which carry tube compressing roller 208, 210 and 212 on suitable bearings disposed on the spindles and within the rollers.

Enclosing the rotor assembly around 180° are the pump halves 174 and 176 as best shown in FIG. 8. The pump halves 174 and 176 have inner surfaces 214 and 214' which cooperatively define a semicircular opening tangentially adjacent the roller assembly between the points 216 and 216' throughout substantially 180° of the rotor assembly. The pump halves separate along a line 218 which intersects the tangency between the pump halves and the rotor assembly substantially 90° between points 216 and 216' as shown at 220 in FIG. 8. The pump halves move toward and away from each other along the lines 222 and are constrained during such motion for conjoint movement diagonally toward and away from the rotor assembly along lines 224 and 226. Lines 224 and 226 lie perpendicular to each other and are parallel to the lines 224' and 226' that dissect the angular distance between the points 216 and 216' and the midpoint 220 in the tangency of the pump halves with the rotor assembly. As a result of the aforesaid movement of the pump halves, the pump tubes 150 and 150' are not stretched between the rotor assembly and the pump halves as the pump halves are closed about the rotor assembly, but rather the tubes are simply compressed as shown in FIG. 8.

Figure 10:
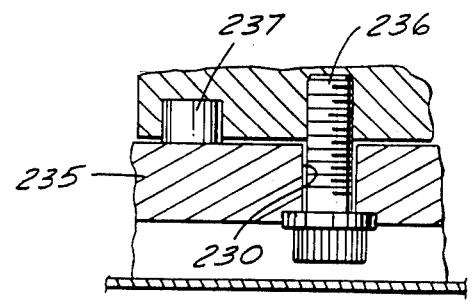
FIG. 10 is a cross sectional view taken substantially on the line 10—10 of FIG. 8.
Figure 11:
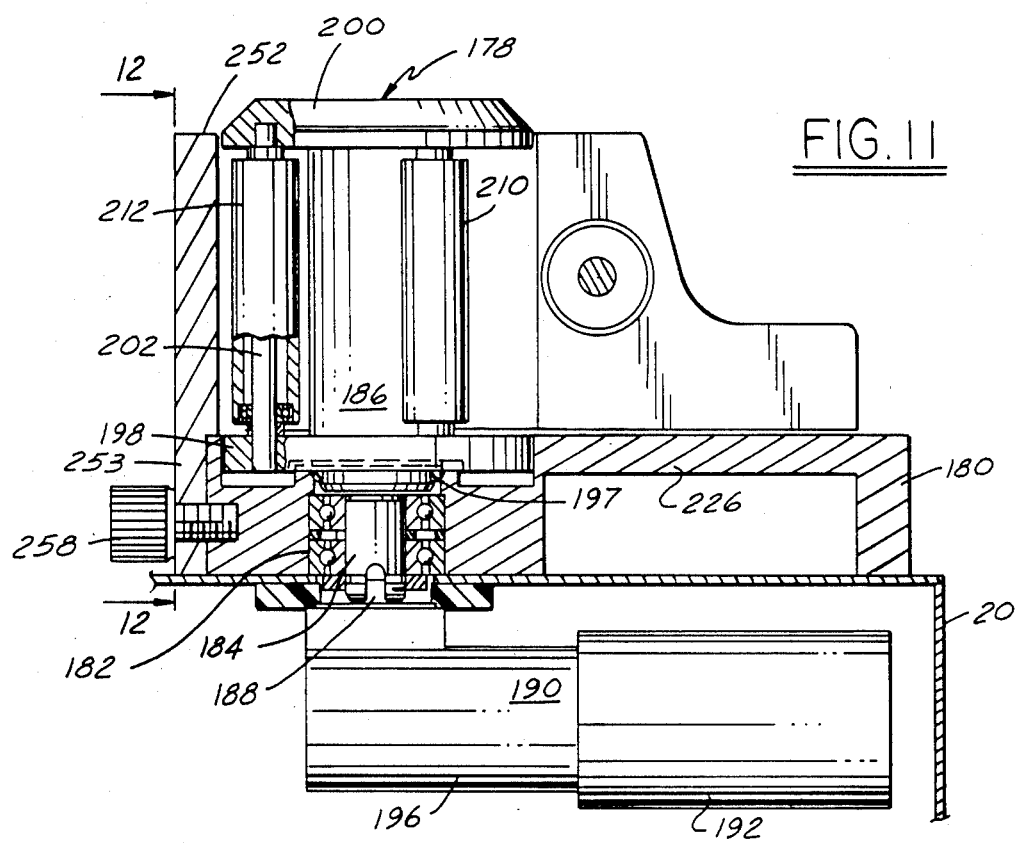
FIG. 11 is a cross sectional view taken substantially on the line 11—11 of FIG. 8.

The pump halves are constrained to move in the aforesaid fashion by angularly related slots 228, 230, 232 and 234 formed in the upper wall 235 of the pump base 180, as shown in FIG. 10. Fasteners 236 extend through the slots and not only serve to hold the pump halves downwardly toward the pump base, but also serve to guide the pump halves in their diagonal motion with respect to the rotor assembly. Shoes 237 received in provided recesses in the pump halves bear against the wall 235 of the base to provide a bearing support for the sliding action of the pump halves on the base.

Figure 9:
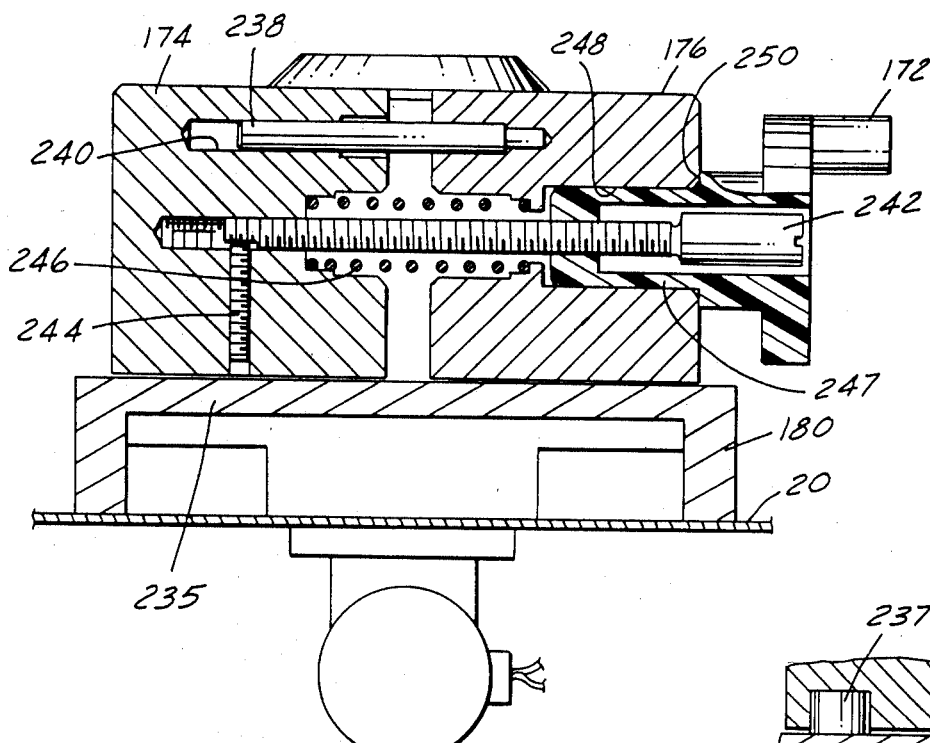
FIG. 9 is a cross sectional view through the pump of FIG. 8 taken substantially on the line 9—9 thereof.

The pump halves 174 and 176 are moved toward and away from each other in the direction of arrows 222 by the mechanism shown in FIG. 9 comprising a guide pin 238 press fitted in the pump half 176 and slidably received in bore 240 in pump half 174. Screw member 242 is threaded at one end into the pump half 174 and locked therein against further rotation by the set screw 244. A compression spring 246 encircles the screw 242 and bears at opposite ends against the pump halves to urge them apart. The crank 172 has a hollow bearing sleeve portion 247 which is threadedly connected with the screw 242 and is journaled within the bore 248 in pump half 176. The crank includes an abutment shoulder 250 bearing against the pump half 176 whereby upon rotating the crank in one direction the pump halves are drawn together while counter rotation allows compression spring 246 to urge the pump halves apart.

Figure 13:
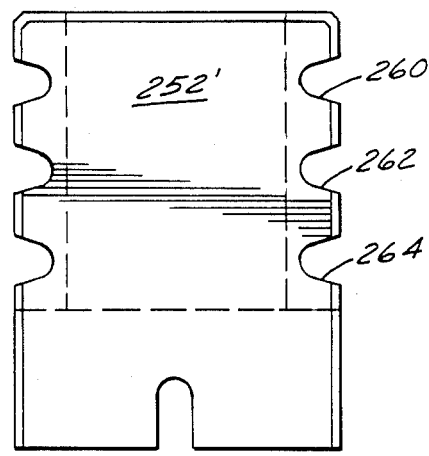
FIG. 13 is a view similar to FIG. 12 but showing the pump adapted for three pumping tubes, rather than two.

Located at the open side 249 of the rotor enclosing pocket defined by the pump halves is a removably mounted pump tube positioner 252 which is generally U-shaped in plan view as shown in FIG. 8, with the legs of the U-shape provided with two pairs of tube positioning notches 254 and 254' and 256 and 256', as shown in FIG. 12. The positioner 252 provided with a tongue-like extension 253 overlying the front of the pump base 180 through which extends a threaded fastener 258 to hold the positioner to the base. The positioner may be readily removed by removal of the fastener 258 for servicing the pump or to replace the positioner with one containing more or fewer pairs of tube positioning notches. For example, in FIG. 13 is shown a positioner having three pairs of notches, namely, 260, 262 and 264, to accommodate three pumping tubes should, for any reason, such be desirable. It will be noted that the pump itself between the pump halves and the rotor assembly may accommodate as many tubes as may be fitted therebetween. The tube positioner 252 or 252' serves to hold the pump tubes in position between the rotor assembly and the pump halves. Thus, it will be seen that a nonpulsatile rotor pump is provided which is extremely simple to load with the tubes or to unload, all without disassembly of the pump and without contaminating the tubes. The pump unit is relatively small and rugged and may provide for one or more tubes to permit pumping to one or a plurality of organs.

Figure 15:
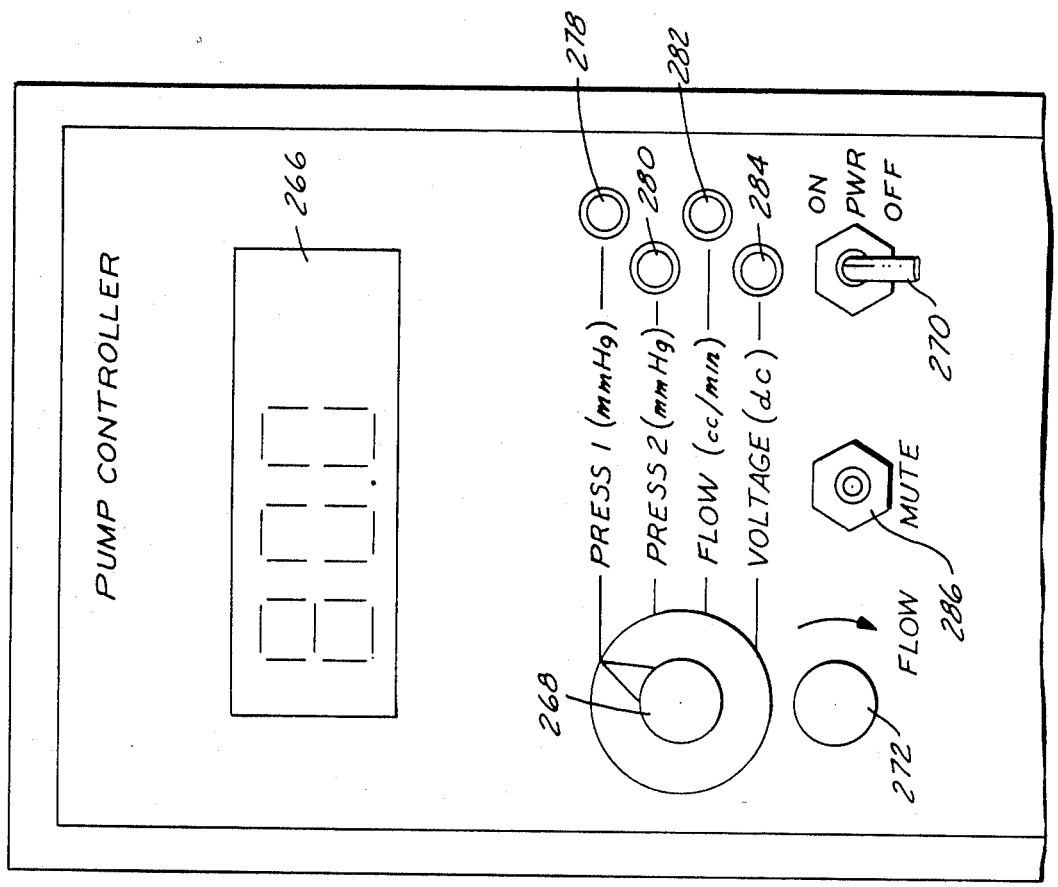
FIG. 15 is a plan view of the pump controller keyboard shown at the right front of FIG. 1.
Figure 16A:
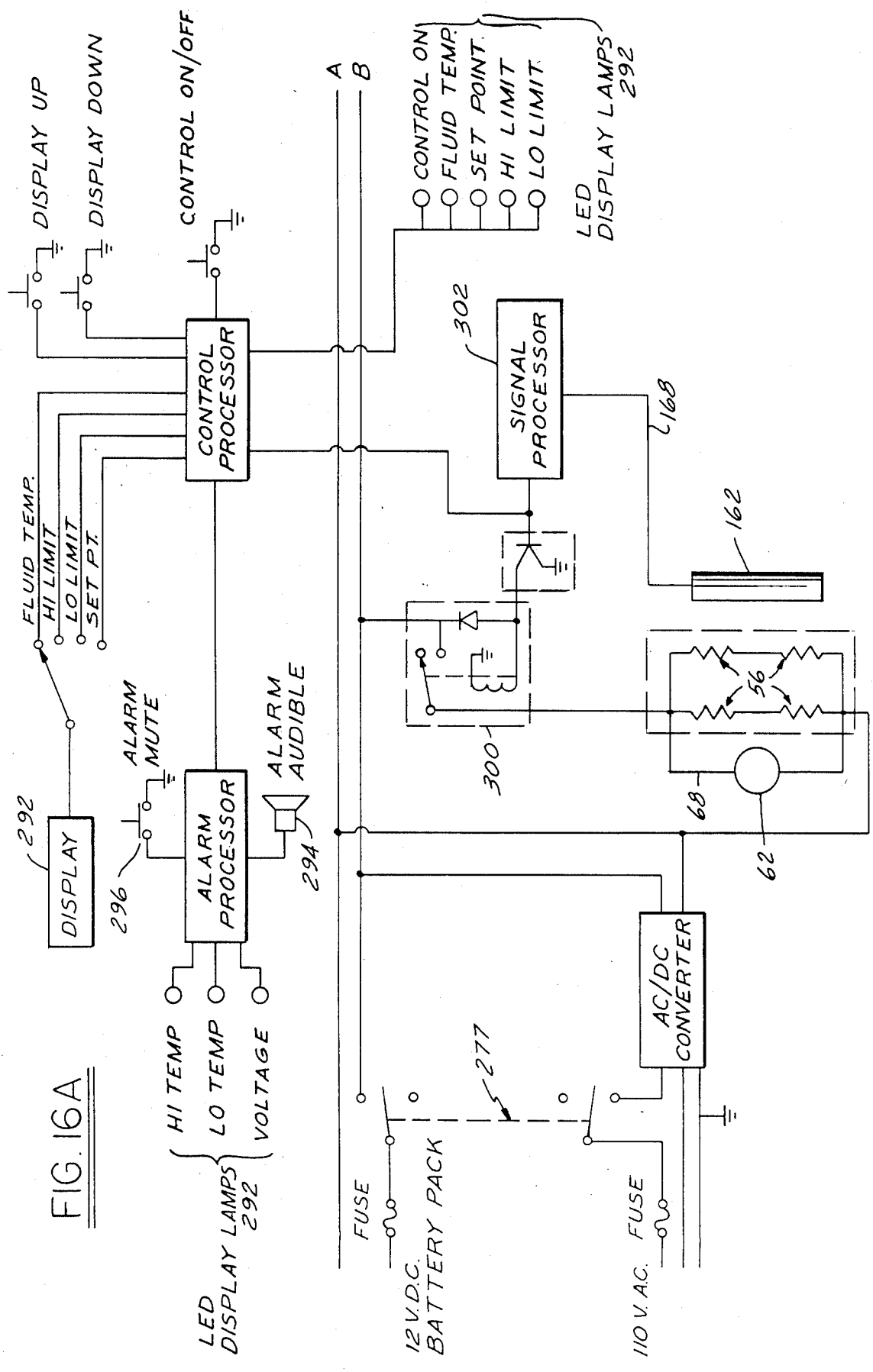

FIGS. 16A and 16B schematically shows the microprocessor circuitry of the machine whose explanation of operation is generally described hereinafter and should suffice for one skilled in the art to construct the necessary circuitry. Pump speed (and in turn flow rate) and perfusate pressure are controlled and displayed in the pump controller shown in FIGS. 15 and 16B wherein a digital display module 266 is connected selectively by the mode switch 268 to one of four circuits as shown particularly in FIG. 16B. In the position shown, the display is connected to read the pressure in line 160', but may be switched to PRESS 2 to read the pressure in line 160. Desirably, the pressure is read as millimeters of mercury.

By moving switch 268 to a third position, the flow rate may be monitored as a function of pump rotor speed and in a fourth position the voltage at the output of the internal power supply 194 may be noted, which would be of importance when the machine is operating on a battery pack. Conductors A and B of FIG. 16B are intended to be connected to a 12 V DC battery pack as shown in FIG. 16A. An AC to DC converter may be connected to conductors A and B if the machine is to be connected to a 110 V AC source. An isolation switch 277 of conventional construction may be provided for this purpose.

Pump operation is initiated by first switching on the pump power switch 270 which activates the display 266. Precise fine control of the pump may be achieved by manually rotating the flow control 272 which adjusts the SPEED CONTROL of FIG. 16B. Modes available for display are voltage (reading in volts DC), flow (reading in cc per minute), where the display value is for a single tube and is based on rotational speed of the rotor assembly. When operating with two tubes, the actual flow is then twice the displayed value. Pressure, as previously mentioned, will be read in millimeters of mercury, and either the pressure in lines 160 or 160' may be displayed. Each of these modes is automatically monitored for failure. A failure activates an alarm processor 274. Should pressure, flow rate or voltage fall below or exceed a pre-set amount, the alarm 274 is activated. Thus, if the pressure falls below 10 mm of mercury or exceeds 100 mm of mercury, in either line 160 or 160', the audible alarm 276 will be sounded and lights 278 or 280 illuminated. Similarly, the voltage alarm and light 284 are activated whenever the voltage drops below 11.25 VDC. Should the flow rate vary by more than its allowed amount, the light 282 will be illuminated and audible alarm 276 sounded. The audible alarm may be silenced by the mute switch 286. The lights 278–284 will remain energized until the failure is corrected within acceptable limits. The pump speed, and in turn the flow rate and pressure, is controlled within the aforementioned limits by the pump controller, such that the speed of the pump motor 192 is determined and monitored by the system of FIG. 16B and will be increased or decreased by the speed control 287.

Figure 14:
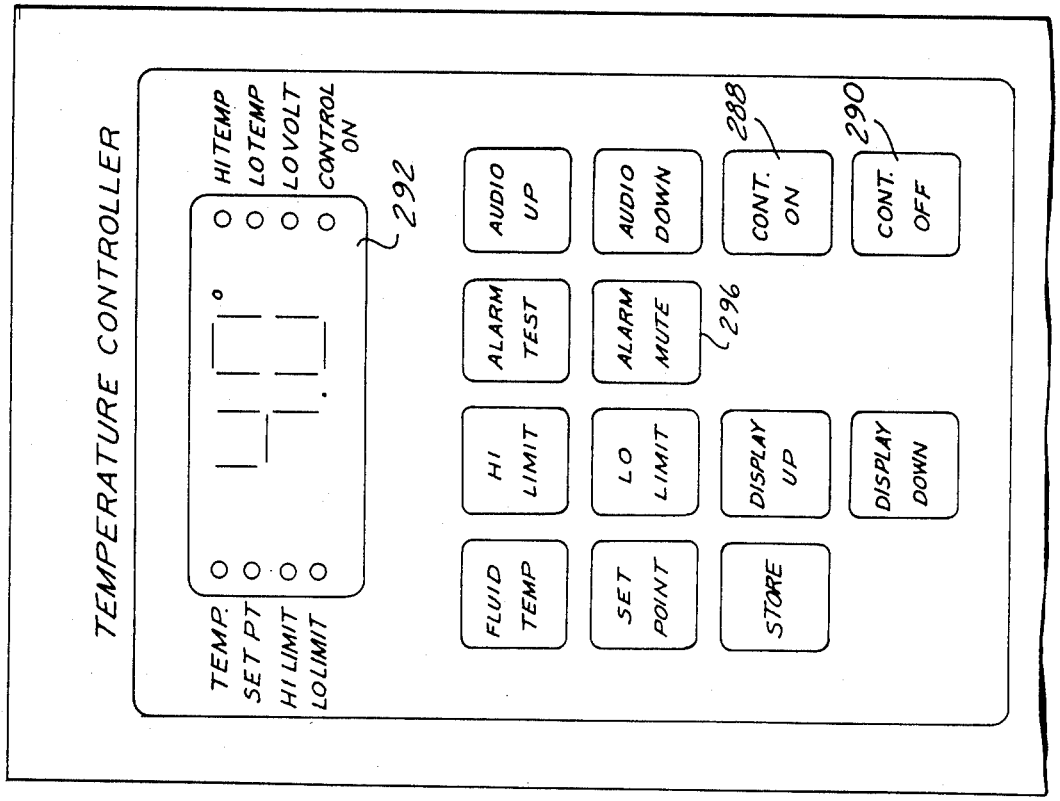
FIG. 14 is a plan view of the temperature controller keyboard shown at the left front of the machine in FIG. 1.

As above indicated, perfusate temperature is sensed by the sensor 162. The cold plate 30 temperature is controlled from the temperature controller panel shown in FIG. 14. Control is initiated by depressing the membrane switch 288, or operation is discontinued by depressing the membrane switch 290. The controller utilizes a microprocessor. Shortly after depressing switch 288, the microprocessor will perform a system check by lighting all light emitting diodes of the display 292. Thereafter, the cooling modules are energized. The temperature at the probe 162 is then automatically displayed at 292 and will change as the temperature of the perfusate as sensed at 162 varies.

The control panel provides for setting the desired perfusate temperature (termed "SET POINT" on the panel) and the lower and upper temperature alarm limits (termed "LO LIMIT" and "HI LIMIT" on the panel). The limits and the set point may be changed by incrementing or decrementing the display by operating the "DISPLAY UP" or "DISPLAY DOWN" membrane switches. The desired value is stored by pressing the "STORE" switch.

Until the actual perfusate temperature reaches the upper limit, the HI TEMP LED remains lit. When the actual perfusate temperature is within the acceptable range, the light is shut off. When the temperature exceeds either the lower or upper limit, the audible alarm 294 sounds and the appropriate alarm LED flashes. The audible alarm may be muted by depressing the MUTE pad, switch 296. The LED will stop flashing but will remain lit as long as the temperature is out of the limits. Of course, the microprocessor controller through the relay 300 will open or close the circuit to the thermoelectric modules 56 in accordance with whether the system is calling for cooling as determined by the signal processor 302.

A prototype machine constructed as above described, weighed approximately 45 lbs. and is fully manually portable either by one or two persons. It is capable of maintaining a perfusate temperature of 4° C. at a room ambient temperature (outside the enclosure) up to 25° C.

We claim:

1. Apparatus for maintaining extracorporeal organs in a viable state during transportation and storage comprising, in combination:

a readily manually transportable insulated enclosure including separable cover and base portions;

means for releasably securing the base and cover portions together;

a perfusate reservoir in the enclosure;

thermoelectric means in the base portion for cooling the reservoir and interior of the enclosure;

means in the enclosure for supporting an organ for perfusing;

means in the enclosure for directing perfusate expelled from the organ to the perfusate reservoir;

a perfusate pump on the base portion for fluid connection between the reservoir and an organ supported within the enclosure;

control means including means for sensing the temperature and pressure of perfusate being pumped, said control means being connected to said pump and to said thermoelectric means for varying the operation of the pump and thermoelectric means to maintain the temperature and flow or pressure of the perfusate being pumped within predetermined limits; and wherein said thermoelectric means includes a cooling plate supported in an upwardly facing position on the baes portion, and means supporting the perfusate reservoir in direct heat transfer juxtaposition atop the cooling plate.

2. The invention defined by claim 1 characterized in that the perfusate pump is disposed on the base portion outside of said enclosure.

3. The invention defined by claim 1 wherein said control means includes alarm means connected to said sensing meeans for signalling variation of perfusate temperature or pressure beyond predetermined limits.

4. The invention defined by claim 1 wherein said control means includes means for setting temperature limits to include upper, lower and control set point.

5. The invention defined by claim 1 wherein said control means includes means for adjusting the perfusate flow rate and operable to disually display the same.

6. The invention defined by claim 1 wherein said control means includes display means for visually displaying temperature of the perfusate being pumped.

7. The invention defined by claim 1 wherein said control means includes display means for visually displaying pressure of the perfusate being pumped.

8. The invention defined by claim 1 wherein said control means includes alarm means for signalling variations of perfusate flow rate beyond predetermined limits.

9. The invention defined by claim 1 wherein said thermoelectric means comprise a plurality of Peltier effect modules disposed on the base, each such module having a cool side and a warm side, and means in the hollow base for transferring heat from the warm side of the modules to the exterior of the hollow base.

10. The invention defined by claim 1 wherein there is a heat sink cooling plate on said hollow base for heat transfer juxtapositioned against the reservoir and against said Peltier effect modules.

11. The invention defined by claim 1 wherein said control means includes alarm means connected to said sensing means for signalling variation of perfusate temperature, flow, pressure and supply voltage beyond predetermined limits.

12. Apparatus for maintaining extracoporeal organs in a viable state during transportation and storage comprising, in combination;
a readily manually transportable insulated enclosure including a separable cover and base portions;
means for releasably securing the base and cover portions together;
a perfusate reservoir in the enclosure;
thermoelectric means in the base portion for cooling the reservoir and interior of the enclosure;
means in the enclosure for supporting an organ for perfusing;
means in the enclosure for directing perfusate expelled from the organ to the perfusate reservoir;
a perfusate pump on the base portion for fluid connection between the reservoir and an organ supported within the enclosure;
control means including means for sensing the temperature and pressure of perfusate being pumped, said control means being connected to said pump and to said thermoelectric means for varying the operation of the pump and thermoelectric means to maintain the temperature and flow or pressure of the perfusate being pumped within predetermined limits; and
wherein said base portion includes a console portion disposed outside said enclosure including a pump control display and a temperature control display.

13. Apparatus for maintaining extracorporeal organs in a viable state during transportation and storage comprising, in combination:
a readily manually transportable insulated enclosure including separable cover and base portions;
means for releasably securing the base and cover portions together;
a perfusate reservoir in the enclosure;
thermoelectric means in the base portion for cooling the reservoir and interor of the enclosure;
means in the enclosure for supporting an organ for perfusing;
means in the enclosure for directing perfusate expelled from the organ to the perfusate reservoir;
a perfusate pump on the base portion for fluid connection between the reservoir and an organ supported within the enclosure;
control means including means for sensing the temperature and pressure of perfusate being pumped, said control means being connected to said pump and to said thermoelectric means for varying the operation of the pump and thermoelectric means to maintain the temperature and flow or pressure of the perfusate being pumped within predetermined limits; and
wherein said perfusate reservoir includes a pair of individual reservoirs and said means for supporting an organ comprises means for supporting one organ above each reservoir, and said pump includes separate pumping chambers for each reservoir and organ, said chambers comprising flexible pump tubes for connection between the reservoir and the respective organ.

14. Apparatus for maintaining extracorporeal organs in a viable state during transportation and storage comprising, in combination:
a readily manually transportable insulated enclosure including separable cover and base portions;
means for releasably securing the base and cover portions together;
a perfusate reservoir in the enclosure;
thermoelectric means in the base portion for cooling the reservoir and interior of the enclosure;
means in the enclosure for supporting an organ for perfusing;
means in the enclosure for directing perfusate expelled from the organ to the perfusate reservoir;
a perfusate pump on the base portion for fluid connection between the reservoir and an organ supported within the enclosure;
control means including means for sensing the temperature and pressure of perfusate being pumped, said control means being connected to said pump and to said thermoelectric means for varying the operation of the pump and thermoelectric means to maintain the temperature and flow or pressure of the perfusate being pumped within predetermined limits; and wherein means are provided in the hollow base for connection to either a source of low voltage direct current or a source of 110 V alternating current and for converting the latter to a low voltage direct current for supplying the pump and thermoelectric means.

* * * * *